United States Patent [19]
Cheng et al.

[11] Patent Number: 5,804,567
[45] Date of Patent: Sep. 8, 1998

[54] METHOD OF INCREASING THE EFFECTIVENESS OF ANTI-METABOLITES

[75] Inventors: Shu Jun Cheng; De Chang Wang; Yong Su Zhen, all of Beijing, China; Hoyoku Nishino, Hirakata; Yukihiko Hara, Fujieda, all of Japan

[73] Assignees: Cancer Institute (Hospital), Chinese Academy of Medical Sciences; Institute of Medicinal Biotechnology, Chinese Academy of Medical Sciences, both of Beijing, China; Mitsui Norin Co., Ltd., Tokyo, Japan

[21] Appl. No.: 919,716

[22] Filed: Aug. 27, 1997

Related U.S. Application Data

[63] Continuation-in-part of Ser. No. 770,553, Dec. 23, 1996, abandoned.

[30] Foreign Application Priority Data

Jul. 18, 1996 [JP] Japan ................................ 8-206361

[51] Int. Cl.⁶ .......................... A01N 43/04; A01N 43/16; A61K 31/715; A61K 31/35

[52] U.S. Cl. .............................. 514/49; 514/50; 514/453; 514/454; 514/456; 549/399; 549/406; 560/544; 560/70

[58] Field of Search ..................................... 549/399, 406; 514/453, 456, 49, 50, 454; 560/544, 70

[56] References Cited

U.S. PATENT DOCUMENTS

| | | | |
|---|---|---|---|
| 5,391,568 | 2/1995 | Chung | 514/456 |
| 5,605,929 | 2/1997 | Liao et al. | 514/456 |

*Primary Examiner*—Sheela Huff
*Attorney, Agent, or Firm*—Frishauf, Holtz, Goodman, Langer & Chick, P.C.

[57] ABSTRACT

A method for treating cancer in a patient by administering to a patient an anti-cancer effective amount of an anti-metabolite selected from the group consisting of 1-β-arabinofuranosylcytosine and 4-amino-4-deoxy-10-methylfolic acid and an anti-oxidant effective amount of a tea polyphenol compound selected from the group consisting of a tea catechin, a theaflavin and a combination of a tea catechin and a theaflavin.

22 Claims, No Drawings

METHOD OF INCREASING THE EFFECTIVENESS OF ANTI-METABOLITES

This application is a continuation-in-part application of application Ser. No. 08/770,553, filed Dec. 23, 1996 now abandoned.

FIELD OF THE INVENTION

The present invention relates to a method of increasing the efficacy of cancer drugs, more specifically it relates to a method of increasing the efficacy of cancer drugs by combining and administering tea catechins and/or theaflavins at the same time as the administration of the cancer drugs.

BACKGROUND OF THE INVENTION

Cancer drugs administered to patients undergo oxidation in the body, and thus their effectiveness is reduced or eliminated. Also some types of cancer drugs produce active oxygen during metabolic processes and this can cause damage to the tissue of normal organs, causing some patients to suffer greatly from the side-effects.

With these points in mind we conducted research into a method of increasing the efficacy of cancer drugs, reducing side-effects thereof. One of such methods which has been investigated is to administer an antioxidant at the same time as the administration of the cancer drug. However, up until now these attempts could not have been said to have reached a sufficient level of success.

SUMMARY OF THE INVENTION

The present inventors conducted extensive research into tea polyphenols such as tea catechins and theaflavins which are the dimers of catechins, and have reported that tea polyphenols have a strong antioxidative action, and free radical scavenging action.

As a result of extensive research into the applications of these functions of tea polyphenols, it was discovered that according to the administration of tea polyphenols at the same time as the administration of an anti-metabolite which is one type of cancer drug, the action of the cancer drug is strengthened, and thus the present invention was completed.

That is to say, the present invention relates to a method of increasing the efficacy of a cancer drug by the addition of tea catechins and/or theaflavins to the cancer drug.

DETAILED DESCRIPTION OF THE INVENTION

The cancer drugs which are applicable to the method of the present invention are not restricted, and in particular chemical cancer drugs are given as preferable examples, but amongst these anti-metabolites are most suitable. Anti-metabolites are compounds which act antagonistically on the metabolism of the purine base or the pyrimidine base, such as cytarabine, methotrexate, 6-mercaptopurine, 5-fluorouracil etc., but among these cytarabine (1-β-D-arabinofuranosylcytosine: Ara-C) or methotrexate (4-amino-4-deoxy-10-methylfolic acid: MTX) are suitable.

The tea polyphenols used in the present invention may be tea catechins or theaflavins obtained by extraction of green tea leaves, black tea leaves etc. with water or organic solvents such as low-grade alcohol, acetone, ethyl acetate, and these may be further separated, purified and used individually or two or more may be combined and used.

Tea catechins are of the general formula I as shown below.

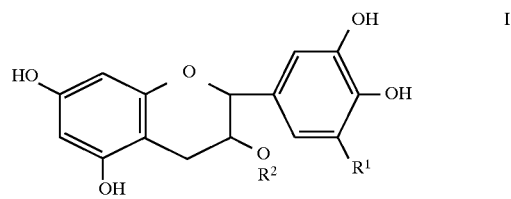

where $R^1$ represents H or OH, and $R^2$ represents H or

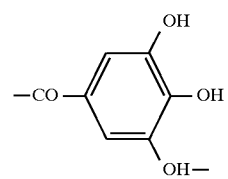

Specifically tea catechins include epicatechin, epicatechin gallate, epigallocatechin, epigallocatechin gallate, gallocatechin etc. (and their derivatives) and these may be used separately or a combination of two or more may be used. Among these, it is desirable that at least one of the following: epigallocatechin gallate, epicatechin gallate and epigallocatechin, is used. In particular it is desirable that a tea catechin wherein epigallocatechin gallate is a main catechin component; as in for example, Polyphenon 100™ (Mitsui Norin Co., Ltd., Composition: (−)epicatechin, 10.8%, (−)epigallocatechin 9.2%, (−)epicatechin gallate 6.5%, (−)epigallocatechin gallate 54.8%, (−) gallocatechin gallate 4.0%) or Polyphenon 60™ (Mitsui Norin Co., Ltd., Composition: (−)epigallocatechin 21.0%, (−)epicatechin, 7.3%, (−) epigallocatechin gallate 29.2%, (−)epicatechin gallate 7.9%)

Theaflavins used in the present invention are of the general formula II as shown below.

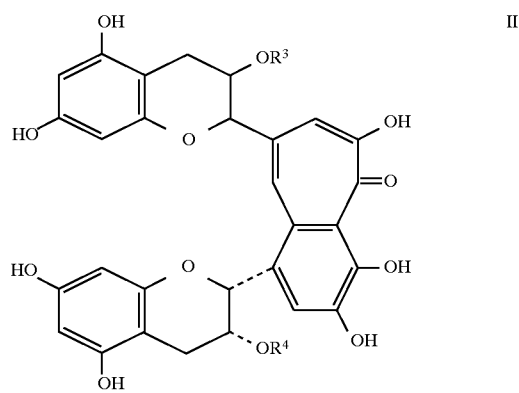

(where $R^3$ and $R^4$ represents H or

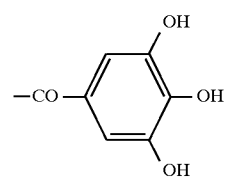

and $R^3$ and $R^4$ may be the same or different).

Specifically, theaflavins include free theaflavins, theaflavin monogallate A, theaflavin monogallate B, theaflavin digallate etc. (and their derivatives), and these may be used individually, or two or more may be combined and used. In particular, desirable is a theaflavin containing theaflavin digallate as a main component; as in for example, Polyphenon TF™ (Mitsui Norin Co., Ltd., Composition: theaflavin 16.8%, theaflavin monogallate A 19.5%, theaflavin monogallate B 16.1%, theaflavin digallate 31.4%) may be used.

According to the present invention, the efficacy of cancer drugs can be strengthened by the addition of tea catechins and/or theaflavins at the same time as the administration of the above-mentioned cancer drugs.

The ratio of the cancer drug to the tea catechin and/or theaflavin should be decided according to the purpose of use, the method of administration of the drug and the type of cancer drug etc., but generally an amount of the cancer drug should be 1–20 mg/kg in case of intraperitoneal administration (i.p.), or more desirably, 5–15 mg/kg (i.p.), and an amount of the tea catechin and/or theaflavin should be 1–30 mg/kg in case of intraperitoneal administration (i.p.), or more desirably, 5–20 mg/kg (i.p.) or 100–1000 mg/kg in case of oral administration (p.o.), wherein "kg" refers to the weight of the patient.

According to the method of the present invention, to increase the efficacy of cancer drugs, tea catechins and/or theaflavins should be administered to patients in the ratios as described above. This mixture can be administered to patients in various forms. For example, it may be combined with a suitable excipient and can be used in an oral and/or non-oral form. A suitable amount of an auxiliary compound such as a lubricant, an emulsifier, a dispersing agent may be used.

As an oral administration, it may be in the form of a liquid, powder, tablet, capsule, granules etc., and in these cases the excipient used apart from water, could be sugars, starch, dextran, calcium phosphate, calcium carbonate, magnesium oxide, magnesium stearate, aluminium silicate, aluminium hydroxide, sodium carbonate, glycerol etc.

As a non-oral administration, it may be in the form of an injection, a drip, and ointment, and it could be mixed with suitable substances such as distilled water, physiological salt, plant oils such as olive oil, alcohol such as ethanol, and polyethylene glycol.

According to the method of the present invention, the efficacy of cancer drugs is strengthened without any side-effects since the cancer drug, in particular an anti-metabolite is used in combination with tea catechins and/or theaflavins.

EXAMPLES

The present invention will be explained by reference to the following examples.

Example 1

$1.5 \times 10^6$ Leukemia L-1210 tumor cells were administered intraperitoneally to Balb/c mice (18–20 g), the mice were divided into 6 groups (10 mice in each group) and after 24 hours a fixed amount of each type of drug was intraperitoneally administered once a day for a period of seven days.

The average rate of survival of each group and the rate of survival of the drug administered group as compared to the control (T/C(%)) as well as long survival rate (over 60 days) were calculated. The results are shown in Table 1.

TABLE 1

| Group | Dose (mg/kg) | Survival days average (day) ± SD | T/C (%) | Number of survivors (over 60 days) |
|---|---|---|---|---|
| Control | — | 16.1 ± 1.1 | | 0/10 |
| AraC | 10 | 28.7 ± 11.8 | 178 | 1/10 |
| EGCg | 10 | 26.8 ± 4.5 | 166 | 0/10 |
| AraC + EGCg | 10 + 10 | 60.0 ± 0 | 373* | 10/10 |
| EGCg | 20 | 12.8 ± 3.7 | 80 | 0/10 |
| AraC + EGCg | 10 + 20 | 37.3 ± 20.1 | 232* | 4/10 |

*P < 0.01
SD: significant difference

As is evident from the table, administration of a combination of cytarabine (AraC) and epigallocatechin gallate (EGCg) significantly increased the survival rate of the mice, and moreover there was a high survival rate over 60 days. No side-effects were noticed.

Example 2

This example was conducted in the same way as in Example 1 except that the amount of EGCg added was different. Results, as shown in Table 2, show that in this case too, the administration of a combination of cytarabine and epigallocatechin gallate increased the survival rate of the mice and significantly increased the survival rate over 60 days.

TABLE 2

| Group | Dose (mg/kg) | Survival days average (day) ± SD | T/C (%) | Number of survivors (over 60 days) |
|---|---|---|---|---|
| Control | — | 17.8 ± 1.2 | | 0/10 |
| AraC | 10 | 35.3 ± 17.3 | 176 | 2/10 |
| EGCg | 5 | 21.0 ± 5.2 | 118 | 0/10 |
| AraC + EGCg | 10 + 5 | 49.2 ± 17.7 | 275* | 7/10 |
| EGCg | 10 | 21.4 ± 4.7 | 120 | 0/10 |
| AraC + EGCg | 10 + 10 | 60.0 ± 0 | 337* | 10/10 |

*P < 0.01
SD: significant difference

Example 3

This example was carried out in the same way as Example 1 except that the tumor cells used were Leukemia P388. Results are shown in Table 3. As is evident from the table, the survival rate of the mice increased and the survival rate over 60 days was significantly higher according to the administration of a combination of cytarabine and epigallocatechin gallate.

TABLE 3

| Group | Dose (mg/kg) | Survival days average (day) ± SD | T/C (%) | Number of survivors (over 60 days) |
|---|---|---|---|---|
| Control | — | 15.4 ± 0.7 | | 0/10 |
| AraC | 10 | 18.9 ± 1.4 | 123 | 0/10 |
| EGCg | 5 | 18.2 ± 1.3 | 118 | 0/10 |
| AraC + EGCg | 10 + 5 | 35.2 ± 21.3 | 229* | 4/10 |
| EGCg | 10 | 17.7 ± 1.8 | 115 | 0/10 |
| AraC + EGCg | 10 + 10 | 60.0 ± 0 | 390* | 10/10 |

*P < 0.01
SD: significant difference

Example 4

KM mice (26–28 g) were each innoculated subcutaneously with $5 \times 10^8$ Sarcoma tumor cells (S-180), the mice were divided into 5 groups (10 mice in each group), and after 24 hours each drug was administered once a day for a period of seven days. According to the intraperitoneal administration 2 mg/kg of methotrexate (MTX) was administered, and 230 mg/kg or 460 mg/kg of epigallocatechin gallate (EGCg) was administered orally.

24 hours after administration of the last drug, the mice were killed, the weight of the tumors was calculated, and according to the extent of metabolic damage the efficacy of the drugs was calcutated. Results are shown in Table 4. As is evident from the table, the weight of the tumors was significantly decreased by administration of a combination of methotrexate and epigallocatechin gallate.

TABLE 4

Effect of Combination of EGCg and MTX on S180 Tumor in Mice

| Groups | Number of Mice | Dose mg/kg | Tumor Weight g X ± SD | Inhibition | P value |
|---|---|---|---|---|---|
| Control | 10 | | 3.4 ± 1.08 | | |
| MTX | 10 | 2.0 i.pX7 | 2.38 ± 1.00 | 30.0 | 0.1 > P > 0.05# |
| EGCg | 10 | 230 p.oX7 | 2.42 ± 0.61 | 28.8 | <0.05# |
| MTX + EGCg | 10 | 2.0 i.pX7 230 p.oX7 | 1.18 ± 0.46 | 65.3 | <0.01* |
| MTX + EGCg | 10 | 2.0 i.pX7 460 p.oX7 | 1.20 ± 0.60 | 64.7 | <0.01* |

: compare with control
*: compare with MTX
i.p: intraperitoneal administration
p.o: oral administration
SD: standard deviation

What is claimed is:

1. In a method for treating cancer in a patient which comprises administering an effective anti-cancer amount of an anti-metabolite to a patient, the improvement which comprises administering an effective amount of a tea polyphenol compound with the anti-metabolite, the anti-metabolite being selected from the group consisting of 1-β-arabinofuranosylcytosine and 4-amino-4-deoxy-10-methylfolic acid, and the tea polyphenol compound being selected from the group consisting of a tea catechin, a theaflavin and a combination of a tea catechin and a theaflavin.

2. The method of claim 1, wherein the anti-metabolite is 1-β-arabinofuranosylcytosine.

3. The method of claim 1, wherein the anti-metabolite is 4-amino-4-deoxy-10-methylfolic acid.

4. The method of claim 1, wherein the tea polyphenol is at least one tea catechin selected from the group consisting of epigallocatechin gallate, epicatechin gallate and epigallocatechin.

5. The method of claim 1, wherein the tea polyphenol is epigallocatechin gallate.

6. The method of claim 1, wherein the tea polyphenol is theaflavin digallate.

7. The method of claim 2, wherein the tea polyphenol is at least one tea catechin selected from the group consisting of epigallocatechin gallate, epicatechin gallate and epigallocatechin.

8. The method of claim 2, wherein the tea polyphenol is epigallocatechin gallate.

9. The method of claim 2, wherein the tea polyphenol is theaflavin digallate.

10. The method of claim 3, wherein the tea polyphenol is at least one tea catechin selected from the group consisting of epigallocatechin gallate, epicatechin gallate and epigallocatechin.

11. The method of claim 3, wherein the tea polyphenol is epigallocatechin gallate.

12. The method of claim 3, wherein the tea polyphenol is theaflavin digallate.

13. The method of claim 1, wherein the anti-metabolite is administered intraperitoneally in an amount of 1 to 20 mg/kg and the tea polyphenol is administered intraperitoneally in an amount of 1 to 30 mg/kg.

14. The method of claim 13, wherein the anti-metabolite is administered in an amount of 5 to 15 mg/kg and the tea polyphenol is administered in an amount of 5 to 20 mg/kg.

15. The method of claim 1, wherein the anti-metabolite is administered intraperitoneally in an amount of 1 to 20 mg/kg and the tea polyphenol is administered orally in an amount of 100 to 1000 mg/kg.

16. The method of claim 15, wherein the tea polyphenol is a tea catechin.

17. The method of claim 15, wherein the tea polyphenol is a theaflavin.

18. The method of claim 15, wherein the tea polyphenol is at least one tea catechin selected from the group consisting of epigallocatechin gallate, epicatechin gallate and epigallocatechin.

19. The method of claim 15, wherein the tea polyphenol is theaflavin digallate.

20. An anti-metabolite-containing composition which consists essentially of an anti-cancer effective amount of an anti-metabolite selected from the group consisting of 1-β-arabinofuranosylcytosine and 4-amino-4-deoxy-10-methylfolic acid, and an effective amount of a tea polyphenol selected from the group consisting of a tea catechin, a theaflavin and a combination of a tea catechin and a theaflavin.

21. The anti-metabolite-containing composition of claim 20, wherein the anti-metabolite is 1-β-arabinofuranosylcytosine and the tea polyphenol is at least one tea catechin or theaflavin selected from the group consisting of epigallocatechin gallate, epicatechin gallate, epigallocatechin and theaflavin digallate.

22. The anti-metabolite-containing composition of claim 20, wherein the anti-metabolite is 4-amino-4-deoxy-10-methylfolic acid and the tea polyphenol is at least one tea catechin or theaflavin selected from the group consisting of epigallocatechin gallate, epicatechin gallate, epigallocatechin and theaflavin digallate.

* * * * *